(12) United States Patent
Hunter

(10) Patent No.: US 10,968,720 B2
(45) Date of Patent: Apr. 6, 2021

(54) DOWNHOLE DEVICES, ASSOCIATED APPARATUS AND METHODS

(71) Applicant: Swellfix UK Limited, Aberdeen (GB)

(72) Inventor: John Hunter, Westhill (GB)

(73) Assignee: SWELLFIX UK LIMITED, Aberdeenshire (GB)

( * ) Notice: Subject to any disclaimer, the term of this patent is extended or adjusted under 35 U.S.C. 154(b) by 70 days.

(21) Appl. No.: 16/340,866

(22) PCT Filed: Oct. 11, 2017

(86) PCT No.: PCT/GB2017/053068
§ 371 (c)(1),
(2) Date: Apr. 10, 2019

(87) PCT Pub. No.: WO2018/069696
PCT Pub. Date: Apr. 19, 2018

(65) Prior Publication Data
US 2019/0242213 A1    Aug. 8, 2019

(30) Foreign Application Priority Data

Oct. 11, 2016    (GB) .................................... 1617234

(51) Int. Cl.
*E21B 34/06*    (2006.01)
*E21B 47/125*    (2012.01)
(Continued)

(52) U.S. Cl.
CPC ........ *E21B 34/066* (2013.01); *E21B 41/0085* (2013.01); *E21B 47/125* (2020.05);
(Continued)

(58) Field of Classification Search
CPC .... E21B 34/066; E21B 47/113; E21B 47/125; E21B 34/063; E21B 49/08;
(Continued)

(56) References Cited

U.S. PATENT DOCUMENTS 3,750,751 A * 8/1973 Mott ..................... E21B 34/102
166/321
8,714,239 B2 * 5/2014 Tosi .................... E21B 41/0085
166/65.1
(Continued)

FOREIGN PATENT DOCUMENTS

WO    WO-2015094147 A1    6/2015

OTHER PUBLICATIONS

International Preliminary Report and Written Opinion for PCT/GB2017/053068 dated Apr. 25, 2019.
(Continued)

*Primary Examiner* — Michael R Wills, III
(74) *Attorney, Agent, or Firm* — Harness, Dickey & Pierce, P.L.C.

(57) ABSTRACT

There are described downhole devices, methods and other apparatus, which may be used to generate energy, monitor fluids and/or provide control signals or otherwise trigger for actuation. The devices, methods, etc. may provide improved autonomy and/or accuracy, while at the same time minimise any effect on the operation of a well. Such devices and methods may be particularly useful downhole and in remote locations. An example of a device comprises a generating material having a fluid contact surface, that contact surface being configured to be in contact with a fluid downhole. The generating material may be configured to generate an electric charge at the material in response a fluid at the contact surface. In some examples, the device further comprises a signal source configured to provide a signal in response to a generated electric charge at the generating material.

19 Claims, 5 Drawing Sheets

(51) Int. Cl.
*E21B 41/00* (2006.01)
*G01N 33/28* (2006.01)
*H02N 1/04* (2006.01)
*E21B 49/08* (2006.01)
*E21B 43/08* (2006.01)
*G01N 13/02* (2006.01)

(52) U.S. Cl.
CPC ........... *G01N 33/2823* (2013.01); *H02N 1/04* (2013.01); *E21B 34/063* (2013.01); *E21B 43/08* (2013.01); *E21B 49/08* (2013.01); *E21B 49/0875* (2020.05); *G01N 13/02* (2013.01); *G01N 2013/0216* (2013.01)

(58) Field of Classification Search
CPC .. E21B 41/0085; E21B 49/0875; E21B 43/08; E21B 47/10; E21B 49/087; E21B 2034/002; E21B 2034/007; E21B 34/14; G01N 13/02; G01N 33/2823; G01N 2013/0216; G01N 27/60; G01V 3/18; H02N 1/04
See application file for complete search history.

(56) References Cited

U.S. PATENT DOCUMENTS

| | | | | |
|---|---|---|---|---|
| 10,305,396 | B1* | 5/2019 | Saraf | H02N 2/0075 |
| 2007/0289739 | A1* | 12/2007 | Cooper | G01F 1/00 |
| | | | | 166/250.01 |
| 2009/0101329 | A1* | 4/2009 | Clem | E21B 43/12 |
| | | | | 166/66.6 |
| 2011/0210645 | A1* | 9/2011 | Mason | H02N 3/00 |
| | | | | 310/309 |
| 2012/0228876 | A1 | 9/2012 | Samuel | |
| 2012/0273234 | A1 | 11/2012 | Tosi et al. | |
| 2016/0258290 | A1* | 9/2016 | Murphree | E21B 43/12 |
| 2017/0306725 | A1* | 10/2017 | Hunter | E21B 41/0085 |

OTHER PUBLICATIONS

International Search Report PCT/ISA/210 for International Application No. PCT/GB2017/053068 dated Dec. 15, 2017.
Written Opinion of the International Searching Authority PCT/ISA/237 for International Application No. PCT/GB2017/053068 dated Dec. 15, 2017.

* cited by examiner

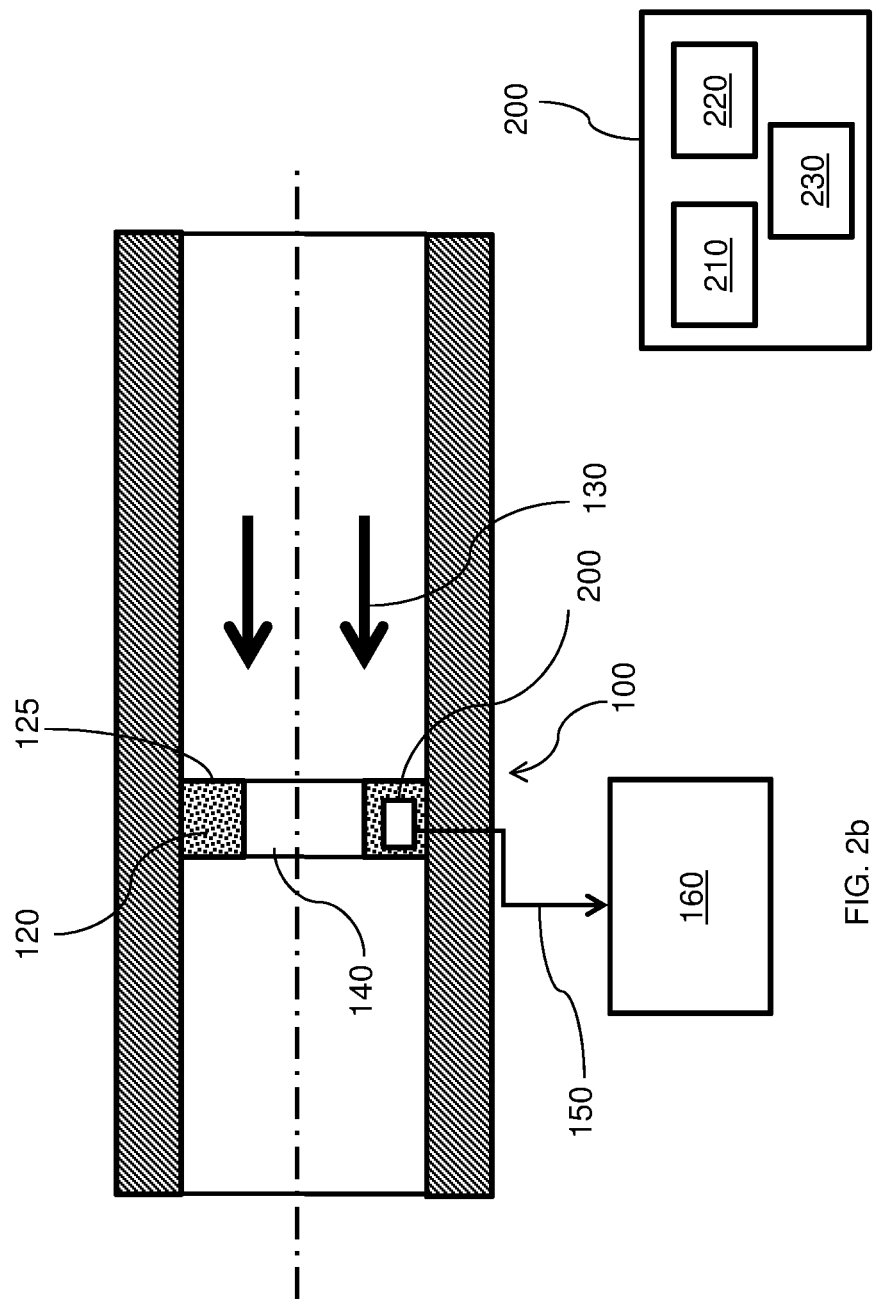

DOWNHOLE DEVICES, ASSOCIATED APPARATUS AND METHODS

CROSS-REFERENCE TO RELATED APPLICATIONS

This application is a national phase under 35 U.S.C. § 371 of PCT International Application No. PCT/GB2017/053068 which has an International filing date of Oct. 11, 2017, which claims priority to British Patent Application No. 1617234.8, filed Oct. 11, 2016, the entire contents of each of which are hereby incorporated by reference.

FIELD

Some described examples relate to downhole devices, associated apparatus and methods. In some cases, those devices, etc., are specifically for use in an oil and gas environment and perform downhole tasks, such as monitoring fluids, generating energy, signalling and the like.

BACKGROUND

In the oil and gas industry there is a continuing desire to improve the understanding and ultimately control the composition of fluids being produced. To manage the production of water, downhole devices have been developed that allow for the inflow of formation fluids at various section of a well to be controlled. In some cases, such inflow control is provided in order to reduce or minimise the production of water.

Inflow control devices (ICDs) may be activated by a control signal or specified activation sequence, or the like. In other examples, such inflow control devices are configured to activate autonomously (AICDs). For such autonomous devices, typically the ability with which fluid can flow through such control devices is affected by the composition or state of that fluid.

Such autonomous devices may be preferred in some applications because they obviate the need for operational user input, or continual monitoring and response to varying production conditions, etc. That said, there is a continuing need to improve the ability with which such flow control devices can operate autonomously and/or with improved accuracy, especially when they are to be installed in remote locations.

Similarly, not least of all in those remote locations, there is a continuing desire to be able to minimise energy usage or at least be able to harvest energy so as to power downhole sensors, equipment, etc., with minimum effect on the operation of a well.

Further still, there is a continuing desire to develop improved devices, methods and techniques for measuring properties of fluids, particularly downhole and in remote locations.

SUMMARY

In some of the following described examples there is provided downhole devices, methods and other apparatus, which may be used to generate energy, monitor fluids and/or provide control signals or otherwise trigger for actuation. The devices, methods, etc. may provide improved autonomy and/or accuracy, while at the same time minimise any effect on the operation of a well. Such devices and method may be particularly useful downhole and in remote locations.

In some examples the devices, methods, etc. may use a generating material having a fluid contact surface. Such a contact surface may be being configured to be in contact with a fluid downhole, for example a flowing fluid. The generating material may be configured to generate an electric charge at the material in response a fluid at the contact surface (e.g. flowing fluid). As such, the device may further comprise a signal source configured to provide a signal in response to a generated electric charge at the generating material.

The generating material may be configured to generate an electric charge in response to a fluid at the contact surface. For example, the generating material may be configured to generate triboelectric charge in response to a fluid at the contact surface, e.g. flowing fluid. The generating material may be configured to generate surface charge in response to fluid at the contact surface. The generating material may be configured to generate an electric charge in response to a fluid at the contact surface using multiple charge effects.

In some examples, the signal source may be configured to provide a fluid monitoring signal, e.g. a data signal or otherwise signal intended to communicate information, in response to a generated electric charge at the generating material. In those examples, the contact surface may be configured to be in contact with a fluid to be monitored. In which case, the generating material may be configured to generate an electric charge in response to a property to be monitored of a fluid at the contact surface. As such, the fluid monitoring signal may correspond to those "to-be-monitored" fluid properties of the fluid at the contact surface.

For example, the device may be specifically configured to monitor for one expected fluid property. In such cases, the generating material may be specifically selected/configured based on that expected fluid property to be monitored. A signal from the signal source may provide information relating to the measurement—or otherwise monitoring—of that fluid property in the fluid at the contact surface.

In some examples given, the device may be specifically configured to monitor for the presence (or indeed the extent of the presence) of a constituent fluid of a fluid at the contact surface. For example, that constituent fluid to be monitored may be one of water, oil or gas—as may be expected in a production well, for example. In some cases, the device may be specifically configured to monitor for (or otherwise measure) the water cut, i.e. percentage of water composition, of any fluid flowing at the contact surface. The signal source may be configured to provide a fluid monitoring signal in response to a generated electric charge at the generating material corresponding to the water cut of the fluid.

In some other examples, however, the device may be configured additionally or alternatively to monitor other fluid properties, such as temperatures, pressures, flow rates, viscosities, pH, etc. Such properties may be used for flow metering, or the like.

The generating material may comprise one or more defined flow paths along which fluid can flow against, or otherwise be in contact with, the contact surface. The flow path(s) may comprise channels formed through the generating material, and through which fluid can flow. The channels may be defined by regular and/or irregular structures in the material, such as structured tubes, and/or interstitially connected voids or the like (e.g. open cells).

The generating material may be formed, or comprise micro/nanomaterials or structures, for example nanotubes, particles (e.g. agglomerated particles), or the like. Some or all of the channels may have a narrowest cross-sectional area of in the range of 1 $nm^2$ to 1 $mm^2$. Depending on application, the channels may have an effective length of from around 10 mm to 50 mm or the like, or indeed longer. The generating material may have an effective contact surface area of around 1 m², or greater.

The flow paths may be formed so as to provide a maximum area of contact surface, e.g. for a minimum or an acceptable pressure drop across the device, or indeed generating material (e.g. for an expected fluid flowing at the contact surface). The device may comprise a plurality of alternatively structured flow paths through that material, which may help optimise the contact surface area, while reducing pressure drop.

The generating material may have an effective permeability and/or porosity that is similar to or the same as a well formation in the region at which the device is expected to be positioned. The generating material may comprise silica (e.g. comprising silica particulates). The silica particulates may be formed in a complementary manner to an expected formation at the intended location for the device.

In some examples, the generating material may comprise a single charge-generating material based on intended application. Otherwise, the generating material may comprise multiple charge-generating materials. In those cases, each of the charge generating materials may be configured to provide different charge in response to fluid properties at the contact surface (e.g. different charge for different fluid properties).

The generating material may be specifically configured to communicate electrically-generated charge from the material to one or more conduction paths for further use (e.g. for use at the signal output). In some examples, the conduction paths may be formed solely or principally within the generating material, while in other examples the conduction paths may be formed when fluid is flowing or otherwise present at the contact surface. In other similar words, the device may be specifically configured such that fluid may form part of the conduction path for charge from the generating material.

A signal may be provided directly from electric charge generated as a result of fluid at the contact surface (e.g. a current signal directly from any conduction path). In some examples, the signal may relate to accumulated charge potential in the material. In other similar words, and in either scenario, the signal source may directly use the charge being generated in the generating material for the purposes of a signal. Otherwise, the device may comprise a charge storage device (e.g. battery, capacitor, etc.) configured to provide power to the signal source from time to time, e.g. upon request.

In some examples, the device may comprise a processor module. The processor module may be configured to receive or measure electric charge being generated in the material, and to provide signal (e.g. a data signal, such as a fluid monitoring signal) to the signal source for further communication. In such examples, the processor module may comprise a processor, memory, etc. configured in a known manner. The processor module may comprise a power source. In some examples, the processor module may comprise an amplifier or the like.

It will be appreciated that whether the signal provided at the signal source is directly provided from charge generated at the material (e.g. a current signal) or whether the signal is initially processed, then in either case the signal may comprise information relating to the fluid properties of the fluid at the contact surface.

That signal may be communicated to a further location (e.g. surface), or otherwise that signal may be communicated for further use downhole.

In some cases, the device may be configured to generate energy downhole. In those examples in which the device is configured to provide a power signal, the generating material may be configured (e.g. optimally configured) to generate the electric charge based on the expected fluid properties/conditions downhole. The device may be configured such that electric charge generated at the generating material is permitted to flow (e.g. directly flow) to the signal source so as to provide a power signal. That power signal may be usable to provide power to a further downhole device, and/or a power supply (e.g. a battery), or the like. In those examples, the signal may be communicated to a power storage device. Such a power storage device may comprise a battery, such a trickle charge battery, or capacitor, or the like. In some examples, the downhole device may comprise that downhole power storage device.

The downhole device may comprise a downhole mechanism, tool, or the like, in communication with the signal source. That mechanism may be configured to operate responsive to signals being provided from the signal source. For example, the device may be configured to provide a control signal (e.g. the signal source may provide a trigger signal for the downhole mechanism when a particular generated electric charge indicates certain fluid properties).

The downhole mechanism may comprise a flow control mechanism. The flow control mechanism may be configured to operate (e.g. activate/deactivate) on the basis of a signal being provided at the signal source and in response to a generated electric charge at the generating material.

The flow control mechanism may comprise a valve member configured to control fluid flow by increasing, reducing, initiating and/or discontinuing a flow of flowing fluid. The valve member may be operable between an open position in which flow is permitted and a closed position in which the flow is inhibited or prevented from flowing.

In a closed position, the valve member may be positioned or retained against a valve seat in order to seal and prevent fluid flow. However, it will be appreciated that the flow control mechanism may be configured to partially open or close the valve member in order to restrict flow (e.g. choke).

In some examples, flow control mechanism may comprise an activation device. The activation device may be in communication with the signal source. The activation device may be configured to operate (e.g. open/close) the valve member in the event of a particular signal being received from the signal source. The activation device may comprise an energisable element (e.g. switch, magnet, or the like) configured to retain/release the valve to a particular position. The activation device may comprise a retainer, configured to retain the valve in a particular configuration. The activation device may be configured to activate upon receipt of a particular signal from the signal source. Activation of the activation device may allow the valve member to move between open and closed positions.

The activation device may comprise a biasing mechanism, configured to assist with operable opening/closing of the valve member in the event of a received signal from the signal source. In some examples, the biasing mechanism may comprise a spring, or the like, in order to urge the valve member to an open or closed position accordingly. In some cases, the device may be configured such that, flow of charge from the signal source—which may directly generated from the generating material—may be used to activate the activation device. For example, the activation device may comprise an electrically conducting portion. Current (e.g. the flow of electrical charge) from the signal output may be configured to pass through the conducting portion. When the rate of charge flowing through the conducting portion exceeds at particular threshold, the structural integrity of that portion of the activation device may decrease to an extent to allow the valve to open/close. The activation device may comprise a sacrificial element configured to retain the valve in a particular position In some examples, the biasing mechanism and sacrificial element may be specifically configured together to cause opening/closing of the valve member when a particular threshold current is provided or exceeded from the signal source. That threshold may relate to a particular monitored fluid property (e.g. water cut). In other words, the device may be configured such that when the fluid property is observed, the flow control mechanism operates.

In some examples, the flow control mechanism may be configured as a flapper valve or the like. In such examples, the operable closing of the value may restrict or inhibit flow along a tubing (e.g. producing tubing).

In other examples, the flow control mechanism may be configured as an inflow control device (e.g. together with wellbore completion, or the like). In those examples, operable closing of the value may restrict or inhibit flow from a wellbore or annulus to the production tubing. In such examples, the flow control mechanism may be provided in a housing having an inlet in fluid communication with the wellbore or annulus and an outlet in fluid communication with tubing. The generating material may be provided at the inlet such that fluid flowing over the contact surface of the generating material, to the tubing, via the flow control mechanism. A filter, such as a sandscreen or the like, may be provided upstream of the generating material.

In some further examples, the device may comprise an activation inhibitor. Such an activation inhibitor may prevent fluid be it, or otherwise flowing over, the contact surface. Such an activation inhibitor may be configured to provide a time-delay for activation, e.g. after deployment. Such inhibitor may be removed via intervention means.

In some examples, there is desired a method for use downhole.

The method may comprise providing fluid at a contact surface of a generating material so as to generate an electric charge in response that fluid. The method may comprise providing a signal in response to a generated electric charge at the generating material.

The method may comprise generating a triboelectric charge in response to a fluid at the contact surface, e.g. flowing fluid at the contact surface. The method may comprise generating surface charge in response to fluid at the contact surface. The method may comprise generating an electric charge in response to a fluid at the contact surface using multiple charge effects.

The method may comprise providing a fluid monitoring signal in response to a generated electric charge at the generating material. In those examples, the contact surface may be configured to be in contact with a fluid to be monitored. In which case, the generating material may be configured to generate an electric charge in response to a property of a fluid at the contact surface. As such, the fluid monitoring signal may correspond to fluid properties of the fluid at the contact surface.

In some examples, the method may comprise additionally or alternatively providing a power signal in response to a generated electric charge at the generating material. That power signal may be usable to provide power to a further downhole device, and/or a power supply (e.g. a trickle-charge battery), or the like.

In some examples, the method may comprise activing a downhole mechanism in response to receipt of a signal (e.g. triggering a downhole mechanism). That downhole mechanism may comprise a flow control mechanism.

In some examples, there is described a downhole device comprising:

a generating material having a fluid contact surface, that surface being configured to be in contact with a fluid downhole, and the generating material being configured to generate an electric charge at the material in response a fluid at the contact surface; the device further comprising a signal source configured to provide a signal in response to a generated electric charge at the generating material.

In some examples, there is described a downhole method comprising:

providing fluid at a contact surface of a generating material so as to generate an electric charge in response that fluid;

providing a signal downhole in response to a generated electric charge at the generating material.

The invention includes one or more corresponding aspects, embodiments or features in isolation or in various combinations whether or not specifically stated (including claimed) in that combination or in isolation. As will be appreciated, features associated with particular recited embodiments relating to devices may be equally appropriate as features of embodiments relating specifically to methods of operation or use, and vice versa.

It will be appreciated that one or more embodiments/aspects may be useful in effective monitoring fluids, generating energy, providing downhole control (e.g. autonomous control) and the like.

The above summary is intended to be merely exemplary and non-limiting.

BRIEF DESCRIPTION OF THE DRAWINGS

A description is now given, by way of example only, with reference to the accompanying drawings, in which:—

FIGS. 2a and 2b are examples of a downhole device, and FIG. 2c is an example of a processor module for use with the device of FIG. 2b;

DETAILED DESCRIPTION OF THE DRAWINGS

For ease of explanation, the following examples have been described with reference to oil and gas production wells. However, it will readily be appreciated that the devices and methods described herein may be equally used and may be applicable in respect of injections wells or the like, or other oil and gas infrastructures (particularly remote infrastructures). Similarly, while the following examples may be described in relation to such oil and gas wells, it will be appreciated that the same devices and methods, etc., may be used beyond oil and gas applications. A skilled reader will readily be able to implement those various alternative embodiments accordingly.

Figure 1:
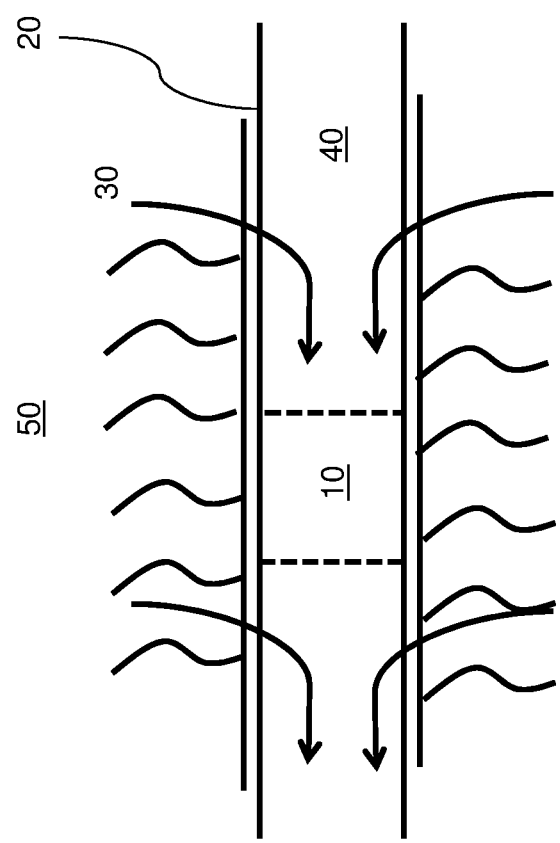
FIG. 1 is a diagrammatic illustration of a portion of a well.

FIG. 1 shows a simplified representation of a horizontal section of a completed well 20. Here, production fluids 30 enter a tubular 40 (e.g. production tubing) from a hydrocarbon-bearing formation 50 for communication to surface (not shown for ease).

Commonly, downhole devices 10 are deployed either as part of the completion, or subsequently in order to collect data, perform control operations, or the like.

Typically, such devices 10 are positioned at remote locations (e.g. remote from surface), and there is a continuing desire to be able to minimise energy usage or at least be able to harvest energy so as to power downhole sensors, equipment, etc., with minimum effect on the operation of a well. Further, there is a desire for such devices 10 to be able to operate with improved autonomy and/or accuracy (e.g. when monitoring condition), especially when they are to be installed in such remote locations.

Consider now FIG. 2, which shows an example of a downhole device 100 that may be deployed in a wellbore (e.g. as in FIG. 1). In this example, and by way of illustration only, the device 100 is comprised with a section of production tubing 110 configured to produce fluids to surface, in a known manner. As will be further explained, the device 100 comprises a generating material 120 that is specifically configured to generate electric charge when interacting with the fluid 130 (e.g. product). The material comprises a contact surface that is configured to be in contact with the fluid 130.

Figure 2A:
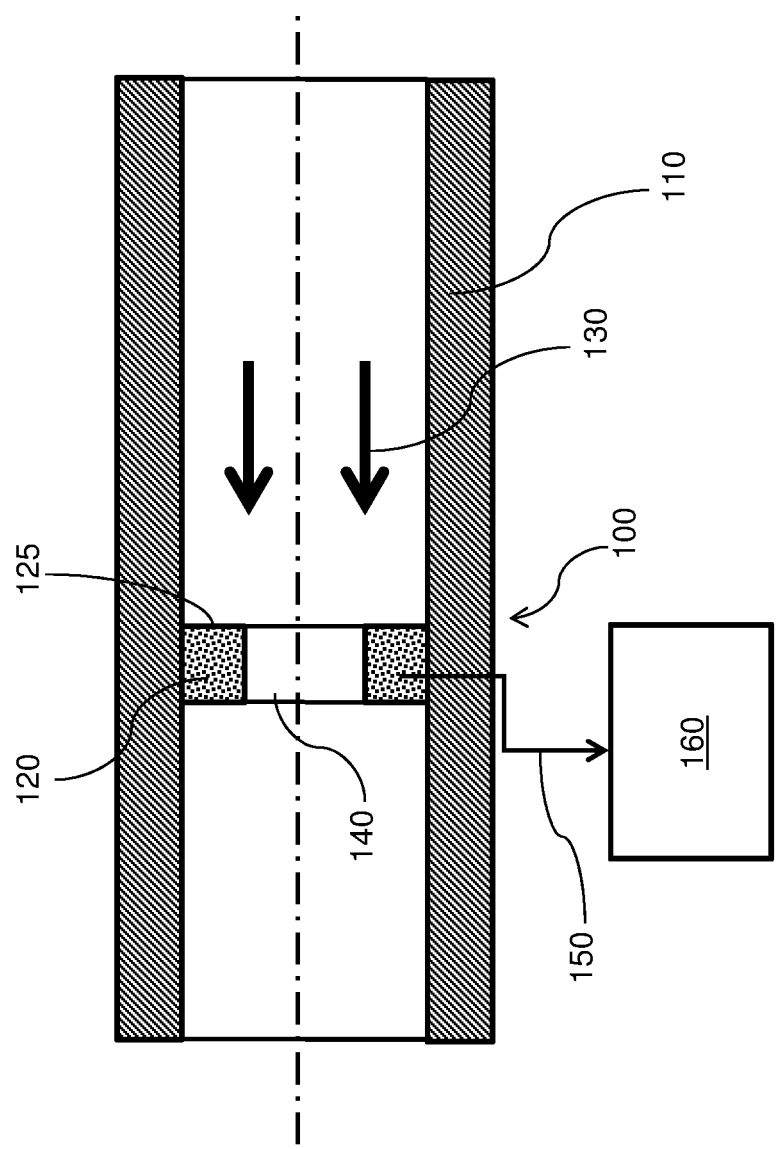

In the example shown in FIG. 2a, the material 120 is formed in annular manner on the inner surface of the tubing 110. As such, an aperture 140 permits some flow of fluid along the tubing 110, without contacting the material 120. In some examples, that need not be the case, and the material 120 may extend entirely across the tubing. It will also be appreciated, given the following description, that in some examples the material 120 may be retained within a support structure, or the like. In other cases, the material may be provided as a coating or the like, for example.

Here, the material 120 itself is formed of, or comprises micro/nanomaterials or structures, for example nanotubes, particles (e.g. agglomerated particles), etc. As such, a number of defined flow paths are provided along which fluid can flow and be in contact with the contact surface. Those flow paths comprise channels formed through the generating material 120 itself, and through which fluid 130 can flow (i.e. in addition to through the aperture 140). The channels 125 may be defined by regular and/or irregular structures in the material, such as structured tubes, and/or interstitially connected voids or the like (e.g. open cells).

In the example shown, the channels may have a narrowest cross-sectional area of in the range of 1 $nm^2$ to 1 $mm^2$. Depending on application, the channels may have an effective length of from around 10 mm to 50 mm or the like, or indeed longer. The effective contact surface area of the generating material may be around 1 $m^2$, or greater.

The flow paths may formed so as to provide a maximum area of contact surface at the material, but for an acceptable pressure drop across the device 100, or indeed generating material 120 (e.g. for an expected fluid flowing at the contact surface).

Here, the material 120 is specifically configured to generate an electric charge, and in this example a triboelectric charge, in response a fluid 130 flowing at the contact surface formed by the flow paths. Of course, this is by example only, and in other embodiments the generating material may be configured to generate surface charge in response to fluid at the contact surface, or indeed be configured to generate an electric charge in response to a fluid at the contact surface using multiple charge effects (e.g. combination of triboelectric, surface, etc.).

In this example however, the flow of fluid across the contact surface generates electric charge within the material 120. The generating material may for example, comprise silica. Some properties of silica may be useful in monitoring for the presence of water. Further, the characteristic properties of silica may be known for downhole environments. That said, other materials may be used as appropriate and depending on application. For example, the material 120 may comprise a single charge-generating material based on intended application, or otherwise comprise multiple charge-generating materials (e.g. as an assembly). In those cases, each of the charge generating materials 120 may be configured to provide different charge in response to fluid properties at the contact surface (e.g. different charge for different fluid properties). Further, those different materials 120 may provide different generating effects (e.g. surface charge, triboelectric, or the like).

It will be appreciated that the generating material 120 may be specifically configured to communicate electrically-generated charge from the material 120 to one or more conduction paths for further use (e.g. for use at a signal output). In some examples, the conduction paths are formed solely or principally within the generating material 120, while in other examples the conduction paths may be formed when fluid is flowing at the contact surface. In other similar words, the flowing fluid may form part of the conduction path for charge from the generating material 120.

In any event, the device 100 further comprises a signal source 150 configured to provide a signal in response to a generated electric charge at the generating material 120 (e.g. and communicated via the conduction paths). That signal may be a power signal and/or data signal (including a control signal), as will be explained.

In this particular case, the signal source 150 is configured to provide a signal directly from any electric charge generated as a result of fluid flowing (e.g. directly from any conduction path). In other similar words, the signal source 150 may be considered to use directly the charge being generated in the generating material 120 for the purposes of a signal.

In circumstances in which the device 100 is configured to provide a power signal, then the generating material 120 may be selected and configured (e.g. optimally configured) to generate the optimal electric charge based on an expected fluid property of the fluid 130. In those examples, the device 100—and the signal source—may be configured to provide a power signal usable to provide power to further downhole devices 160. Such devices 160 may include, for example, downhole mechanisms, actuators, sensors, or indeed power supplies (e.g. batteries). For example, the device 100 may be configured to trickle charge existing downhole power supplies, or systems.

In other examples, the device 100 may be specifically configured to provide a fluid monitoring signal, e.g. a data signal, in response to a generated electric charge at the generating material 120. In which case, the generation material 120 may be configured to generate a particular electric charge in response to a particular property of a fluid flowing at the contact surface. As such, the fluid monitoring signal may correspond to fluid properties of the fluid at the contact surface.

For example, the device 100 can be specifically configured and calibrated to monitor for one expected fluid property, and the components of the device 100 can be selected based on the desired performance of the material for that fluid property, during anticipated operational conditions. In such cases, the generating material 120 may be selected based on that expected fluid property to be monitored. A signal from the signal source 150 can provide information relating to the measurement—or otherwise monitoring—of that fluid property in the fluid at the contact surface.

In the example shown in FIG. 2a, the device 100 is specifically configured to monitor for the presence (or indeed the extent of the presence) of a constituent fluid of a fluid at the contact surface, e.g. water cut—that is the percentage of water composition of any fluid flowing at the contact surface. As such, the output at the signal source 150 (e.g. a current signal or charge held at the material 120) can provide a fluid monitoring signal that corresponds to a generated electric charge at the generating material, which in turn can be related to the water cut of the fluid 130.

It will be appreciated that in some examples, the device 100 can be calibrated for expected water cut (or other fluid property to be monitored) such that the fluid monitoring is provided essentially by the magnitude of the current flow or the observed potential charge stored at the material. That current flow/electric potential can be used as a data signal relating to fluid properties. That data signal may be communicated to surface, and/or other downhole equipment and devices, as needed. In some cases, the signal may be used as a trigger (e.g. when exceeding a particular threshold).

It will be appreciated that in some examples, the device 100 may be configured additionally or alternatively to monitor other fluid properties, such as pressures, temperatures, flow rates, viscosities, pH, etc. Such properties may assist with, or be used in relation to other measurements, such as flow metering, or the like.

It will further be appreciated that while in some examples, current flow/electric potential may be used directly from the material 120, in other examples, the device 100 may comprise a processor module 200 in order to provide the signal to the signal source. Consider now FIG. 2b, which shows the device 100 comprising such a module 200, together with the module 200 itself in FIG. 2c. The processor module 200 may be configured to receive or measure electric charge being generated in the material 120, as above. In such examples, the processor module 200 may comprise a processor 210, memory 220, configured in a known manner. The processor module 200 may comprise a power source 230, as well as other signal processing components as necessary. In a similar manner as before, the signal source may be in communication with further downhole apparatus, or surface, or the like, in order to communicate a data signal relating to the monitoring of fluid. In use, in some examples, charge generated at the material may power the module 200 as well as be used for any subsequent signal.

While in some examples, the device 100 may be used to generate energy for a further downhole device, or provide a data signal for monitoring fluids, etc., in other examples, the device may additionally comprise a downhole mechanism, in communication with the signal source, and configured to operate responsive to signals being provided from the signal source. In such a way, the downhole device 100 may be considered, in some cases, to provide a control signal or otherwise trigger for actuation.

Figure 3:
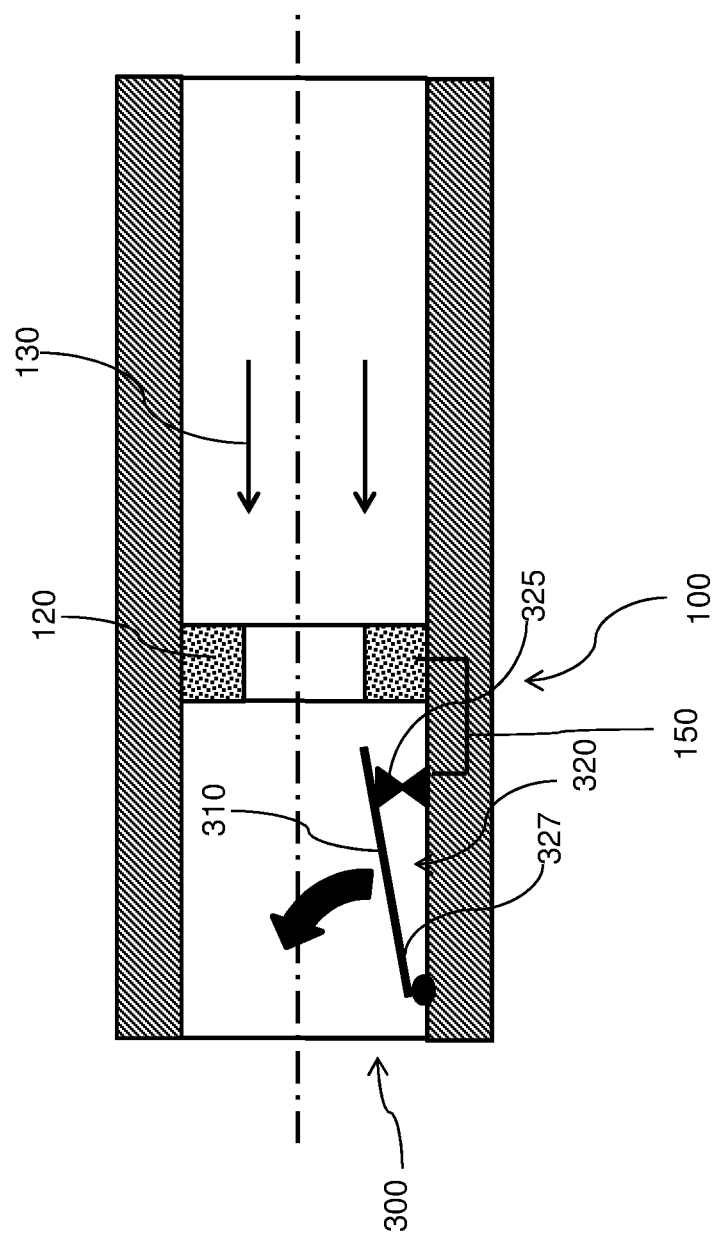
FIG. 3 is an example of the downhole device together with an exemplary downhole mechanism.

Consider now, by way of an example, FIG. 3. Here the device 100 comprises a flow control mechanism 300, which in this case is exemplified as a flapper valve or the like. The signal source 150 is in communication with the flow control mechanism 300 such that the flow control mechanism 300 operates (e.g. activates/deactivates) on the basis of a signal being provided at the signal source 150, and in response to a generated electric charge at the generating material 120.

The flow control mechanism 300 comprises a value member 310 configured to control fluid flow by increasing, reducing, initiating and/or discontinuing a flow of flowing fluid. The valve member 310 is operable between an open position in which flow is permitted and a closed position in which the flow is inhibited or prevented from flowing.

In a closed position, the value member 310 may be positioned or retained against a valve seat (not shown) in order to seal and prevent fluid flow. However, it will be appreciated that the flow control mechanism 300 may be configured to partially open or close the valve member 310 in order to restrict flow (e.g. choke).

In FIG. 3, the flow control mechanism 300 comprises an activation device 320, which is communication with the signal source 150. In this particular case, the activation device 320 may comprise a retainer 325 configured to retain the valve in a particular position (in this case, open). The activation device 320 further comprises a biasing mechanism 327, configured to assist with operable closing of the valve member 310 in the event of a received signal from the signal source. It will be appreciated that the biasing mechanism 327 may comprise a spring, or the like, in order to urge the valve member to an open or closed position accordingly (in this example, closed).

Here, the retainer 325 is specifically configured such that current (e.g. the flow of electrical charge) from the signal output may be configured to pass through a conducting portion of the retainer 325.

When the rate of charge flowing through the conducting portion exceeds at particular threshold, the structural integrity may decrease to an extent to allow the valve to close, using the biasing mechanism 327. As such, the retainer 325 may be considered to be or comprise sacrificial element. The biasing mechanism 327 and retainer 325 may be specifically configured together to cause opening/closing of the valve member 310 when a particular threshold signal is provided or exceeded from the signal source. That threshold may relate to a particular monitored fluid property (e.g. water cut).

Of course, in other examples, the activation device may comprise an energisable element (e.g. magnet) configured to retain/release the valve to a particular position, or the like. Further, the activation device of the fluid control mechanism may be operable using logic signals provided from the signal source.

While in FIG. 3, the fluid control mechanism 300 is shown as a flapper valve, or the like, it will be appreciated that in other examples, the fluid control mechanism 300 may be provided as an inflow control device. In such cases, the downhole device 100 may be provided together with wellbore completion.

Figure 4:
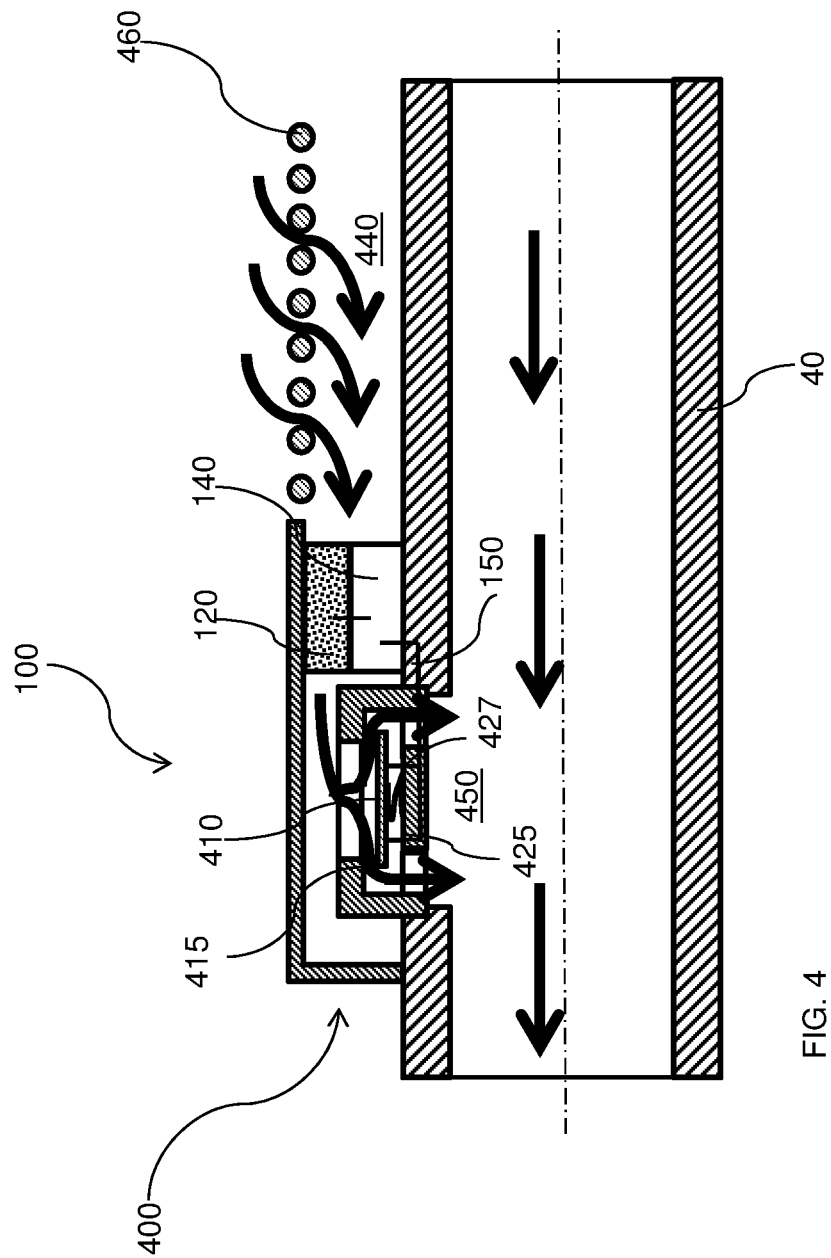
FIG. 4 is a further example of a downhole device together with a further downhole mechanism.

Consider now FIG. 4, which shows a similar downhole device 100, but having an alternative flow control mechanism 400. Here, again the mechanism comprises a valve member 410, in the form of a plate, and a valve seat 415, in order to seal and prevent fluid flow when desired.

Operable closing of the value member 410 can be used restrict or inhibit flow from a wellbore or annulus to the tubing 40. Here, the flow control mechanism 410 is provided in a housing having an inlet 440 in fluid communication with the wellbore and an outlet 450 in fluid communication with tubing 40. In this example, the generating material 120 is provided at the inlet 440 such that fluid flowing from the wellbore flows over the contact surface of the generating material 120, to the tubing 40, via the flow control mechanism 400. A filter 460, such as a sandscreen or the like, may be provided upstream of the generating material 120.

Again, in FIG. 4, the flow control mechanism 400 comprises an activation device 420, which is communication with the signal source 150. In this particular case, the activation device 420 may comprise again retainers 425 (e.g. sacrificial elements, in the form of as a fuses) that are configured to retain the valve member 410 in a particular position (in this case, open). The activation device 420 again further comprises a biasing mechanism 427, configured to assist with operable closing of the valve member 410 in the event of a received signal from the signal source 150. As before, the biasing mechanism 427 and retainer 425 may be specifically configured together to cause opening/closing of the valve member 410 when a particular threshold signal is provided or exceeded from the signal source. That threshold may relate to a particular monitored fluid property (e.g. water cut). As such, the production of water can be accurately and autonomously minimised.

In some of the above examples, the device 100 may comprise an activation inhibitor. Such an activation inhibitor may prevent flow of fluid over the contact surface. Such an activation inhibitor may be configured to provide a time-delay for activation, e.g. after deployment. Such inhibitor may be removed via intervention means.

In the examples above, flowing fluid at the contact surface of the generating material is used to generate an electric charge in response that fluid flowing. From that electric charge, a signal can be provided in response. It some cases, that signal may be used to provide a fluid monitoring signal relating to properties of the fluid, which may be used for data purposes and/or providing a trigger. In further examples, that signal may be usable to provide power to a further downhole device, and/or a power supply (e.g. a trickle-charge battery), or the like.

It will be appreciated that while the above devices have been described in relation to being provided in tubulars, or completions, will be appreciated that the similar devices may be provided in annular spaces between tubulars, as may be desired by some applications. Further, in some examples, the devices may be arranged a linked array, which may help to optimise charge production, and/or assist with accuracy.

Further, and as explained above, while in the examples provided, fluid flowing at the contact surface provides a triboelectric charge in the material for further use, this is by example only, and in other embodiments the generating material may be configured to generate charge as a result of alternative effects or indeed a combination of effects.

The applicant discloses in isolation each individual feature described herein and any combination of two or more such features, to the extent that such features or combinations are capable of being carried out based on the specification as a whole in the light of the common general knowledge of a person skilled in the art, irrespective of whether such features or combinations of features solve any problems disclosed herein, and without limitation to the scope of the claims. The applicant indicates that aspects of the invention may consist of any such individual feature or combination of features. In view of the foregoing description it will be evident to a person skilled in the art that various modifications may be made within the scope of the invention.

The invention claimed is:
1. A downhole device comprising:
   a generating material having a fluid contact surface, that contact surface being configured to be in contact with a fluid downhole, and the generating material being configured to generate an electric charge at the generating material in response a fluid at the contact surface; the device further comprising
   a signal source configured to provide a signal in response to a generated electric charge at the generating material;
   a flow control mechanism in communication with the signal source, the flow control mechanism being configured to operate responsive to signals being provided from the signal source and in response to the generated electric charge at the generating material, wherein the flow control mechanism comprises an activation device, the activation device comprising,
   a retainer configured to retain the flow control mechanism in a particular configuration, and to activate upon receipt of a signal from the signal source so as to release the flow control mechanism, wherein the retainer comprises a conducting sacrificial element configured such that current from the signal passes through the conducting sacrificial element, and further configured such that when a rate of charge flowing through the conducting sacrificial element exceeds a particular threshold, a structural integrity of the conducting sacrificial element decreases to allow activation of the flow control mechanism; and,
   a biasing mechanism configured to assist with operable opening/closing of the flow control mechanism.

2. The device according to claim 1, wherein the generating material is configured to generate at least a triboelectric charge in response a fluid flowing at the contact surface.

3. The device according to claim 1, wherein the signal source is configured to provide a fluid monitoring signal in response to the generated electric charge at the generating material.

4. The device according to claim 3, wherein the device is configured to monitor for an expected fluid property.

5. The device according to claim 3, wherein the device is configured to monitor for a presence of a constituent fluid of a fluid at the contact surface.

6. The device according to claim 5, wherein the device is configured to monitor water composition of fluid at the contact surface.

7. The device according to claim 1, wherein the generating material comprises defined flow paths along which fluid can flow and be in contact with the contact surface.

8. The device according to claim 7, wherein the flow paths comprise channels formed through the generating material, and through which fluid can flow, the formed channels being defined by regular and/or irregular structures in the generating material.

9. The device according to claim 8, wherein the channels comprise nanotubes.

10. The device according to claim 1, wherein the signal source is configured such that the signal is provided directly from the electric charge generated as a result of fluid at the contact surface.

11. The device according to claim 10, wherein the signal source is configured to provide a current signal from the electric charge generated at the generating material, or a charge potential signal relating to the electric charge at the generating material.

12. The device according to claim 1, wherein the device comprises a processor module, the processor module being configured to receive or measure electric charge being generated in the material and to provide signal to the signal source for further communication.

13. The device according to claim 1, wherein the signal source is configured to provide a power signal in response to electric charge being generated at the generating material, that power signal being usable to provide power to a further downhole device and/or a power supply.

14. The device according to claim 11, wherein the device is configured such that the threshold relates to the electric charge expected from a particular fluid property to be monitored.

15. The device according to claim 2, wherein the particular monitored fluid property comprises water cut.

16. The device according to claim 1, wherein the flow control mechanism is configured as an inflow control device together with wellbore completion.

17. The device according to claim 16, wherein the device comprises a filter provided upstream of the generating material.

18. A downhole method comprising:
providing fluid at a contact surface of a generating material so as to generate an electric charge in response that fluid;
providing a signal downhole in response to a generated electric charge at the generating material;
providing a flow control mechanism downhole to receive the signal, the flow control mechanism being configured to operate responsive to the signal provided in response to the generated electric chare at the generating material;
retaining the flow control mechanism in a particular configuration via an activation device, wherein the activation device comprises a retainer, the retainer being a conducting sacrificial element;
activating the activation device upon receipt of the signal;
passing a current though the conducting sacrificial element upon receipt of the signal, wherein the conducting sacrificial element is configured such that when a rate of charge flowing through the element exceeds a particular threshold, a structural integrity of the conducting sacrificial element decreases to allow activation of the flow control mechanism; and,
assisting opening/closing of the flow control mechanism via a biasing mechanism.

19. The method according claim 18, wherein the generating material is configured to generate at least a triboelectric charge in response a fluid flowing at the contact surface.

* * * * *